United States Patent
Momose et al.

(10) Patent No.: US 6,777,435 B1
(45) Date of Patent: Aug. 17, 2004

(54) CRYSTALS OF AN OXYIMINOALKANOIC ACID DERIVATIVE AND THEIR USE AS ANTIDIABETICS

(75) Inventors: Yu Momose, Takarazuka (JP); Hiroshi Imoto, Kusatsu (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 10/111,479

(22) PCT Filed: Oct. 26, 2000

(86) PCT No.: PCT/JP00/07482

§ 371 (c)(1),
(2), (4) Date: Apr. 25, 2002

(87) PCT Pub. No.: WO01/32637

PCT Pub. Date: May 10, 2001

(30) Foreign Application Priority Data

Oct. 29, 1999 (JP) ............................................ 11-308346

(51) Int. Cl.⁷ ...................... A61K 31/42; C07D 263/34
(52) U.S. Cl. ...................................... 514/374; 548/236
(58) Field of Search ........................... 514/374; 548/236

(56) References Cited

U.S. PATENT DOCUMENTS 6,518,435 B1 * 2/2003 Yamane et al. ............. 548/236

FOREIGN PATENT DOCUMENTS

WO 99/58510 11/1999

OTHER PUBLICATIONS

Munzel, K. "Der Einfluss der Formgebung auf die Wirkung eines Arzneimittels", Progres in Drug Research—Fortschritte Der Arzneimittelforschung—Progress Des Recherches Pharmaceutiques, CH, Birkhaeuser Verlag, Basel, vol. 10, 1966, pp. 227–230, XP–002078506, English translation enclosed.

Munzel, K. "Galenische Formgebung und Arznelmittelwirkung/Neue Erkenntnisse und Feststellungen", Progress in Drug Research—Fortschritte Der Arzneimittelforschung—Progress Des Recherches Pharmaceutiques, CH, Birkhaeuser Verlag, Basel, vol. 14, 1970, pp. 309–321, XP–002078507, English translation enclosed.

T. Sohda et al., "Studies on Antidiabetic Agents, 11,' Novel Thiazolidinedione Derivatives as Potent Hypoglycemic and Hypolipidemic Agents", J. Med. Chem., vol. 35, pp. 2617–2626, 1992.

* cited by examiner

Primary Examiner—Deborah Lambkin
(74) Attorney, Agent, or Firm—Wenderoth, Lind & Ponack, L.L.P.

(57) ABSTRACT

Crystals of (E)-4-[4-(5-methyl-2-phenyl-4-oxazolylmethoxy)benzyloxyimino]-4-phenylbutyric acid (provided that crystals having a melting point of 126° C. to 127° C. are excluded), which have an excellent anti-diabetic action.

15 Claims, 3 Drawing Sheets

CRYSTALS OF AN OXYIMINOALKANOIC ACID DERIVATIVE AND THEIR USE AS ANTIDIABETICS

This application a 371 of PCT/JP00/07482 filed Oct. 26, 2000.

TECHNICAL FIELD

The present invention relates to crystals of an oxyiminoalkanoic acid derivative having an anti-diabetic action, to a pharmaceutical composition and a retinoid-related receptor function regulating agent, etc. comprising said crystals.

BACKGROUND ART

In many organic compounds, it has been known that the so-called polymorphism of crystals can occur where the crystal form is different even if the composition is same. With crystal polymorphism, there are cases where physical/chemical properties such as melting point, solubility and stability and biological properties such as pharmacokinetics (absorption, distribution, metabolism, excretion) and pharmacodynamics are different but it is impossible to predict them from the structure of the compound.

There has been a demand in the pharmaceutical industry for crystals having excellent properties as a medicine, such as stable crystals having good absorption.

DISCLOSURE OF INVENTION

As a result of intensive investigation, the present inventors have succeeded in preparing stable crystals of (E)-4-[4-(5-methyl-2-phenyl-4-oxazolylmethoxy)benzyloxyimino]-4-phenylbutyric acid (hereafter also abbreviated as compound A), and found for the first time that these crystals had excellent properties as a medicine (excellent properties as a final medicine and raw material medicine). Based on these findings, the present inventors have completed the present invention.

Namely, the present invention relates to:

(1) crystals of (E)-4-[4-(5-methyl-2-phenyl-4-oxazolylmethoxy)benzyloxyimino]-4-phenylbutyric acid (provided that crystals having a melting point of 126° C. to 127° C. are excluded);

(2) the crystals according to the above (1), which have a melting point of about 136° C. to about 139° C.;

(3) crystals of (E)-4-[4-(5-methyl-2-phenyl-4-oxazolylmethoxy)benzyloxyimino]-4-phenylbutyric acid showing diffraction patterns having characteristic peaks at the spacings (d values) of about 17.5 and about 6.0 Å by a powder x-ray crystal diffraction;

(4) a pharmaceutical composition comprising the crystals of the above (1) or (3);

(5) the pharmaceutical composition according to the above (4), which is an agent for preventing or treating diabetes mellitus;

(6) the pharmaceutical composition according to the above (4), which is an agent for preventing or treating hyperlipemia;

(7) the pharmaceutical composition according to the above (4), which is an agent for preventing or treating impaired glucose tolerance;

(8) the pharmaceutical composition according to the above (4), which is an agent for preventing or treating inflammatory diseases;

(9) the pharmaceutical composition according to the above (4), which is an agent for preventing or treating arteriosclerosis;

(10) a retinoid-related receptor function regulating agent comprising the crystals of the above (1) or (3);

(11) the agent according to the above (10), which is a ligand for peroxisome proliferator-activated receptors;

(12) the agent according to the above (10), which is a ligand for retinoid X receptors;

(13) the pharmaceutical composition according to the above (4), which is an insulin sensitivity enhancing agent;

(14) the pharmaceutical composition according to the above (4), which is an insulin resistance improving agent;

(15) a method for preventing or treating diabetes mellitus in a mammal in need thereof, which comprises administering to said mammal an effective amount of crystals as defined in the above (1) or (3); and (16) use of crystals as defined in the above (1) or (3) for the manufacture of a pharmaceutical preparation for preventing or treating diabetes mellitus.

BEST MODE FOR CARRYING OUT THE INVENTION (1) Production Method

Crystals of (E)-4-[4-(5-methyl-2-phenyl-4-oxazolylmethoxy)benzyloxyimino]-4-phenylbutyric acid (provided that crystals having the melting point of 126° C. to 127° C. are excluded) (hereinafter, sometimes abbreviated as crystals of the present inventions) can be produced by crystallization of compound A by adopting a per se known crystallization method.

Examples of such crystallizing methods include crystallization from a solution, crystallization from vapor and crystallization from a melted substance.

Examples of the "crystallization from a solution" include concentrating methods, gradually cooling methods, reacting methods (diffusing methods, electrolyzing methods), hydrothermal growing methods and flux methods. Examples of the solvent employed include aromatic hydrocarbons (e.g. benzene, toluene, xylene), halogenated hydrocarbons (e.g., dichloromethane, chloroform), saturated hydrocarbons (e.g., hexane, heptane, cyclohexane), ethers (e.g., diethyl ether, diisopropyl ether, tetrahydrofuran, dioxane), nitriles (e.g., acetonitrile), ketones (e.g., acetone), sulfoxides (e.g., dimethyl sulfoxide), acid amides (e.g., N,N-dimethylformamide), esters (e.g., ethylacetate), alcohols (e.g., methanol, ethanol, isopropyl alcohol), and water. These solvents may be used either singly, or as a mixture of two or more species in an appropriate ratio (e.g., 1:1 to 1:100 (volume ratio)).

Examples of the "crystallization from vapor" include vaporizing method (sealed tube method, stream method), gas-phase reacting method and chemically transporting method.

Examples of the "crystallization from a melted substance" include normal freezing method (pulling-up method, temperature inclining method, Bridgman method), zone melting method (zone leveling method, float zone method), special growing method (VLS method, liquid-phase epitaxial method).

For instance, crystallization is carried out by dissolving compound A in an appropriate solvent (e.g., alcohols such as methanol, ethanol, etc.) under the temperature of 20 to 120° C., cooling the resulting solution to the temperature below the temperature at the time of dissolution (e.g., 0 to 50° C., preferably 0 to 20° C.,). The thus obtained crystals can be isolated by filtration etc.

As a method for analyzing the resulting crystals, a method of crystal analysis by means of X-ray diffraction is common. As a method for determining the azimuth of the crystals, mechanical method, optical method, etc. are exemplified.

Compound A can be produced by a per se known method such as the following method which is described in the specification of JP-A 2000-34266 (Japanese Patent Application No. Hei-11/130543, WO99/58510) or a method analogous thereto. Compound A is the same as compound (III) having hydroxyl group for $R^1$ and compound (III').

having 6–10 carbons which may be substituted by an alkyl group having 1–4 carbons" for $R^3$ include methyl, ethyl, propyl, isopropyl, butyl, isobutyl, sec-butyl, tert-butyl. Among them, methyl is preferred.

Examples of the aryl group having 6–10 carbons in "an aryl group having 6–10 carbons which may be substituted by an alkyl group having 1–4 carbons" for $R^3$ include phenyl, naphthyl. Among them, phenyl is preferred.

Examples of the hydrocarbon group in "an optionally substituted hydrocarbon group" for $R^2$ include an aliphatic hydrocarbon group, an alicyclic hydrocarbon group, an aromatic-aliphatic hydrocarbon group, an aromatic hydrocarbon group.

As the aliphatic hydrocarbon group, that having 1–8 carbons is preferred. Examples of the aliphatic hydrocarbon group include saturated aliphatic hydrocarbon groups having 1–8 carbons (e.g., an alkyl group) such as methyl, ethyl, propyl, isopropyl, butyl, isobutyl, sec-butyl, t.-butyl, pentyl, isopentyl, neopentyl, hexyl, isohexyl, heptyl, octyl; and unsaturated aliphatic hydrocarbon groups (e.g., an alkenyl wherein Z is a hydroxyl group, a halogen atom or a group represented by $OSO_2R^3$, where $R^3$ is an alkyl group having 1–4 carbons or an aryl group having 6–10 carbons which may be substituted by an alkyl group having 1–4 carbons; $R^1$ is a hydroxyl group or $-OR^2$, where $R^2$ is an optionally substituted hydrocarbon group.

Here, examples of the alkyl group having 1–4 carbons in "an alkyl group having 1–4 carbons" and "an aryl group group having 2–8 carbons, an alkadienyl group having 4–8 carbons, an alkenylalkynyl group having 2–8 carbons, an alkadlynyl group having 4–8 carbons) such as ethenyl, 1-propenyl, 2-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 3-hexenyl, 2,4-hexadienyl, 5-hexenyl, 1-heptenyl, 1-octenyl, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl, 2,4-hedadiynyl, 5-hexynyl, 1-heptynyl, 1-octynyl.

As the alicyclic hydrocarbon group, that having 3–7 carbons is preferred. Examples of the alicyclic hydrocarbon group include saturated alicyclic hydrocarbon groups having 3–7 carbons (e.g., a cycloalkyl group) such as cyclopropyl, cyclobutyl, cyclopentyl, cyclohexyl. cycloheptyl; unsaturated alicyclic hydrocarbon groups having 5–7 carbons (e.g., a cycloalkenyl group, a cycloalkadienyl group) such as 1-cyclopentenyl, 2-cyclopentenyl, 3-cyclopentyl, 1-cyclohexenyl, 2-cyclohexenyl, 3-cyclohexenyl, 1-cycloheptenyl, 2-cycloheptenyl, 3-cycloheptenyl, 2,4-cycloheptadienyl.

As the aromatic-aliphatic hydrocarbon group, that having 7–13 carbons (e.g., an aralkyl group having 7–13 carbons, an arylalkenyl group having 8–13 carbons) is preferred. Examples of the aromatic-aliphatic hydrocarbon group include phenylalkyl having 7–9 carbons such as benzyl, phenethyl. 1-phenylethyl, 1-phenylpropyl, 2-phenylpropyl, 3-phenylpropyl; a naphthylalkyl having 11–13 carbons such as α-naphthylmethyl, α-naphthylethyl, β-naphthylmethyl, β-naphthylethyl; a phenylalkenyl having 8–10 carbons such as styryl; and a naphthylalkenyl having 12–13 carbons such as 2-(2-naphthylvinyl).

As an aromatic hydrocarbon group, that having 6–14 carbons (e.g., an aryl group) is preferred. Examples of the aromatic hydrocarbon group include phenyl, naphthyl, anthryl, phenanthryl, acenaphthylenyl, biphenylyl. Among them, phenyl, 1-naphthyl, 2-naphthyl are preferred.

$R^2$ is preferably an alkyl group having 1–4 carbons, a phenylalkenyl group having B-10 carbons and an aryl group having 6–14 carbons, each of which may be substituted.

A hydrocarbon group for $R^2$ may have 1–5 or, preferably 1–3 substituents at substitutable positions. Examples of the substituents include a halogen atom (e.g., fluorine, chlorine, bromine, iodine), an alkoxy group having 1–4 carbons (e.g., methoxy, ethoxy, propoxy, isopropoxy, butoxy, isobutoxy, sec.-butoxy, t.-butoxy), an aryloxy group having 6–14 carbons (e.g., phenoxy, naphthyloxy); and an aromatic heterocyclic group (e.g., furyl, thienyl).

In the present method, compound (III) is produced by the reaction of compound (I) with compound (II).

When Z is a hydroxyl group, the reaction may be carried out by a per se known method such as a method described in "Synthesis", page 1 (1981) or a method analogous thereto. Namely, this reaction is usually carried out in a solvent which does not affect the reaction in the presence of an organic phosphorus compound and an electrophilic agent.

Examples of the organic phosphorus compound include triphenyl phosphine, tributyl phosphine.

Examples of the electrophilic agent include diethyl azodicarboxylate, duisopropyl azodicarboxylate, azodicarbonyl dipiperazine.

The amount of the organic phosphorus compound and the electrophilic agent used is preferably 1–5 molar equivalents to compound (II).

Examples of the solvent which does not affect the reaction include ethers such as diethyl ether, tetrahydrofuran, dioxane; halogenated hydrocarbons such as chloroform, dichloromethane; aromatic hydrocarbons such as benzene, toluene, xylene; amides such as N,N-dimethylformamide; and sulfoxides such as dimethyl sulfoxide. These solvents may be used as a mixture in an appropriate ratio.

The reaction temperature is usually −50° C. to 150° C., preferably −10° C. to 100° C. The reaction time is 0.5 to 20 hours.

When Z is a halogen atom or a group represented by $OSO_2R^3$, the reaction is carried out according to a conventional method in the presence of a base in a solvent which does not affect the reaction.

Examples of the base include alkaline metal salts such as potassium hydroxide, sodium hydroxide, sodium bicarbonate, potassium carbonate; amines such as pyridine, triethylamine, N,N-dimethylaniline, 1,8-diazabicyclo[5.4.0]undec-7-ene; metal hydrides such as potassium hydride, sodium hydride; alkaline metal alkoxides such as sodium methoxide, sodium ethoxide, potassium t.-butoxide.

The amount of the base used is preferably 1–5 molar equivalents to compound (II).

Examples of the solvent which does not affect the reaction include aromatic hydrocarbons such as benzene, toluene, xylene; ethers such as tetrahydrofuran, dioxane; ketones such as acetone, 2-butanone; halogenated hydrocarbons such as chloroform, dichloromethane; amides such as N,N-dimethylformamide; sulfoxides such as dimethyl sulfoxide. These solvents may be used as a mixture in an appropriate ratio.

The reaction temperature is usually −50° C. to 150° C., preferably −10° C. to 100° C. The reaction time is usually 0.5 to 20 hours.

After that, compound (III, where $R^1$ is $—OR^2$) is subjected to a hydrolysis reaction if necessary whereupon compound (III') is produced.

This hydrolysis reaction is carried out according to a conventional method in the presence of an acid or a base in an aqueous solvent.

Examples of the acid include hydrochloric acid, sulfuric acid, acetic acid, hydrobromic acid.

Examples of the base include alkaline metal carbonates such as potassium carbonate, sodium carbonate; alkaline metal alkoxides such as sodium methoxide; alkaline metal hydroxides such as potassium hydroxide, sodium hydroxide, lithium hydroxide.

The amount of the acid or the base used is usually in an excess amount to compound (III). Preferably, the amount of the acid used is 2–50 equivalents to compound (III), while that of the base used is 1.2–5 equivalents to compound (III).

Examples of the aqueous solvent include a mixed solvent of one or more solvents selected from alcohols such as methanol, ethanol; ethers such as tetrahydrofuran, dioxane; dimethyl sulfoxide and acetone; and water.

The reaction temperature is usually −20° C. to 150° C., preferably −10° C. to 100° C. The reaction time is usually 0.1 to 20 hours.

Compounds (III) and (III') thus obtained can be isolated and purified by a known separating and purifying means such as concentration, concentration under reduced pressure, extraction with solvent, crystallization, recrystallization, dissolution and chromatography.

Incidentally, compound (I) and compound (II) used as the starting compounds in the above method are known compounds. For example, compound (I) where Z is a hydroxyl group is described in EP-A 710659. Also, compound (I) is described in EP-A 629624 (JP-A Hei-07/53555), WO 98/03505, etc. Further, compound (I) can be produced by a method analogous to those described in these publications.

On the other hand, compound (II) is described, for example, in Journal für praktische Chemie, volume 311, page 370 (1969); Canadian Journal of Chemistry, volume 48, page 1948 (1970); Journal of Heterocyclic Chemistry, volume 25, page 1283 (1988); etc. Further, compound (II) can be produced by a method analogous to those described in those publications.

(2) Salts

Compound A may form a salt. As such salt, a pharmacologically acceptable one is preferred, and its examples include a salt with an inorganic base, a salt with an organic base.

Suitable examples of the salt with an inorganic base include alkaline metal salts such as sodium salt, potassium salt; alkaline earth metal salts such as calcium salt, magnesium salt; aluminum salt; ammonium salt.

Suitable examples of the salt with an organic base include salts with trimethylamine, triethylamine, pyridine, picoline, ethanolamine, diethanolamine, triethanolamine, dicyclohexylamine, N,N-dibenzylethylenediamine.

(3) Properties of the Crystals

The crystals of the present invention are not especially limited so long as they are crystals of compound A and not crystals having a melting point of 126° C. to 127° C. Especially preferred are crystals having a melting point of 130° C. or more, preferably crystals having a melting point of about 136° C. to about 139° C.

As the crystals of the present invention, also mentioned are those showing diffraction patterns having characteristic peaks at the spacings (d values) of about 17.5, about 6.0 Å (preferably about 17.5, about 8.91, about 7.81, about 5.98, about 4.65, about 4.29, about 4.09 and about 3.54 Å) by a powder x-ray crystal diffraction.

The crystals of the present invention are preferably those having a melting point of about 136° C. to about 139° C., and showing diffraction patterns having characteristic peaks at the spacings (d values) of about 17.5, about 6.0 Å (preferably about 17.5, about 8.91, about 7.81, about 5.98, about 4.65, about 4.29, about 4.09 and about 3.54 Å) by a powder x-ray crystal diffraction.

In the present specification, the melting point means, for instance, one determined by using a small amount melting point determination device (Yanako, MP-500D type).

In the present specification, the characteristic peaks by a powder x-ray crystal diffraction means, for instance, peaks determined by using RINT1100 Type (Rigakudenki, Japan) using Cu-K$\alpha_1$ ray (voltage: 40 KV; electric current: 40 mA) as a ray source.

Generally, melting points and characteristic peaks by a powder x-ray crystal diffraction sometimes vary depending on determination devices, determination conditions, etc. The crystals of the present invention may be those showing different values from the above defined melting point or characteristic peaks by a powder x-ray crystal diffraction so long as the values are within normal errors.

The crystals of the present invention are excellent in physical/chemical properties (e.g., melting point, solubility, stability) and biological properties (e.g., pharmacokinetics (absorption, distribution, metabolism, excretion), pharmacodynamics), and therefore, are quite useful as a medicine.

(4) Formulations

The crystals of the present invention have low toxicity and may be used as an agent for preventing or treating various diseases which will be mentioned later in mammals (e.g., human being, mice, rats, rabbits, dogs, cats, cattle, horses, pigs, monkeys) as they are or by processing into a pharmaceutical composition by mixing with a pharmacologically acceptable carrier or the like.

Here, examples of the pharmacologically acceptable carrier include various organic or inorganic carrier substances which are conventionally used as pharmaceutical preparation materials. They are incorporated as exclpients, lubricants, binders, disintegrants in solid preparations; as solvents, solubilizers, suspending agents, isotonizing agents, buffers, local analgesics in liquid preparations. According to necessity, additives such as preservatives, antioxidants, coloring agents and sweeteners may be used.

Preferred examples of the excipients include lactose, sucrose, D-mannitol, D-sorbitol, starch, gelatinized starch, dextrin, crystalline cellulose, low-substituted hydroxypropylcellulose, carboxymethylcellulose sodium, gum arabic, dextrin, pullulan, light silicic anhydride, synthetic aluminum silicate, magnesium aluminometasilicate.

Preferred examples of the lubricants include magnesium stearate, calcium stearate, talc, colloidal silica.

Preferred examples of the binders include gelatinized starch, saccharose, gelatin, gum arabic, methylcellulose, carboxymethylcellulose, carboxymethyicellulose sodium, crystalline cellulose, sucrose, D-mannitol, trehalose, dextrin, pullulan, hydroxypropylcellulose, hydroxypropylmethylcellulose, polyvinylpyrrolidone.

Preferred examples of the disintegrants include lactose, sucrose, starch, carboxymethylcellulose, carboxymethylcellulose calcium, croscarmellose sodium, carboxymethylstarch sodium, light silicic anhydride, low-substituted hydroxypropylcellulose.

Preferred examples of the solvents include water for injection, physiological saline, Ringer's solution, alcohol, propylene glycol, polyethylene glycol, sesame oil, corn oil, olive oil, cotton seed oil, Preferred examples of the solubilizers include polyethylene glycol, propylene glycol, D-mannitol, trehalose, benzyl benzoate, ethanol, trisaminomethane, cholesterol, triethanolamlne, sodium carbonate, sodium citrate, sodium salicylate, sodium acetate.

Preferred examples of the suspending agents include surfactants such as stearyltriethanolamine, sodium lauryl sulfate, laurylaminopropionic acid, lecithin, benzalkonium chloride, benzethonium chloride and glycerol monostearate; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose; polysorbates, polyoxyethylene-hardened castor oil.

Preferred examples of the isotonizing agents include sodium chloride, glycerol, D-mannitol, D-sorbitol, glucose.

Preferred examples of the buffers include buffer solutions of phosphate, acetate, carbonate, citrate.

Preferred examples of the local analgesics include benzyl alcohol.

Preferred examples of the preservatives include para-hydroxybenzoate esters, chlorobutanol, benzyl alcohol, phenethyl alcohol, dehydroacetic acid, sorbic acid.

Preferred examples of the antioxidants include sulfite salts, ascorbate salts.

Preferred examples of the coloring agents include water-soluble colored tar dyes (e.g. food colors such as Food Color Red No. 2 and No. 3, Food Color Yellow No. 4 and No. 5, Food Color Blue No. 1 and No. 2), water-insoluble lake colors (e.g. the aluminum salt form of the above water-soluble edible tar colors), natural colors (e.g. β-carotene, chlorophyll, iron oxide red).

Preferred examples of the sweeteners include saccharin sodium, dipotassium glycyrrhizinate, aspartame, stevia.

(5) Mode of Administration

The dosage forms of a pharmaceutical composition include oral preparations such as tablets, capsules (including soft capsules and microcapsules), granules, powders, syrups, emulsions, suspensions; and non-oral preparations such as injections (e.g. subcutaneous injection, intravenous injection, intramuscular injection, intraperitoneal injection), drip infusions, external application forms (e.g. nasal preparations, transdermal preparations, ointments), suppositories (e.g. rectal suppositories, vaginal suppositories), pellets, solutions for instillation, sustained-release preparations.

The pharmaceutical composition can be produced by conventional methods in the fields of pharmaceutical manufacturing techniques, for example, methods described in the Japanese Pharmacopoeia. In the following, specific methods for producing preparations are described in detail.

An oral preparation, for instance, is produced by adding to the active ingredient an excipient (e.g., lactose, sucrose, starch, D-mannitol), a disintegrant (e.g., carboxymethylcellulose calcium), a binder (e.g., gelatinized starch, gum arabic, carboxymethylcellulose, hydroxypropylcellulose, polyvinylpyrrolidone) or a lubricant (e.g., talc, magnesium stearate, polyethyleneglycol 6000), compression molding the obtained mixture, then, if necessary coating by a per se known method using a coating base for the purpose of taste masking, enteric coating or sustained release.

Examples of the coating base include a sugar coating base, a water-soluble film coating base, an enteric film coating base, a sustained-release film coating base.

As the sugar coating base sucrose is employed. Further, one or two or more species selected from talc, precipitated calcium carbonate, gelatin, gum arabic, pullulan, carnauba wax and the like may be used in combination.

Examples of the water-soluble film coating base include cellulose polymers such as hydroxypropylcellulose, hydroxypropylmethylcellulose, hydroxyethylcellulose, methylhydroxyethylcellulose; synthetic polymers such as polyvinylacetal diethylaminoacetate, aminoalkyl methacrylate copolymer E [Eudragit E (trademark), Rhom Pharma] and polyvinylpyrrolidone; polysaccharides such as pullulan.

Examples of the enteric film coating base include cellulose polymers such as hydroxypropylmethylcellulose phthalate, hydroxypropylmethylcellulose acetate succinate, carboxymethylethylcellulose, cellulose acetate phthalate; acrylic acid polymers such as methacrylic acid copolymer L [Eudragit L (trademark), Rhom Pharma], methacrylic acid copolymer LD [Eudragit L-30D55 (trademark), Rhom Pharma], methacryllc acid copolymer S [Eudragit S (trademark), Rhom Pharma]; natural products such as shellac and the like.

Examples of the sustained-release film coating base include cellulose polymers such as ethylcellulose; acrylic acid polymers such as aminoalkyl methacrylate copolymer RS [Eudragit RS (trademark), Rhom Pharma] and an ethyl acrylate-methyl methacrylate copolymer suspension [Eudragit NE (trademark), Rhom Pharma].

Two or more of the above coating bases may be used in admixture in an appropriate ratio. On the occasion of coating, a shading agent such as titanium oxide, red ferric oxide may be used.

Injections are produced by dissolving, suspending or emulsifying the active ingredient in an aqueous solvent (e.g. distilled water, physiological saline, Ringer's solution) or an oleaginous solvent (e.g. vegetable oils such as olive oil, sesame oil, cotton seed oil, corn oil; propylene glycol), together with a dispersant (e.g. polysorbate 80, polyoxyethylene-hardened castor oil 60), polyethylene glycol, carboxymethylcellulose, sodium alginate), a preservative (e.g. methylparaben, propylparaben, benzyl alcohol, chlorobutanol, phenol), an isotonizing agent (e.g. sodium chloride, glycerol, D-mannitol, D-sorbitol, glucose) and the like. If desirable, additives such as a solubilizer (e.g. sodium salicylate, sodium acetate), a stabilizer (e.g. human serum albumin), an analgesic (e.g. benzyl alcohol), may be used.

(6) Composition, Agent

Another aspect of the present invention is a pharmaceutical composition comprising the crystals of the present invention.

Said pharmaceutical composition can be especially used for prevention or treatment of diabetes mellitus, hyperlipemia, impaired glucose tolerance, inflammatory disease, arteriosclerosis, etc.

The crystals of the present invention can be used as an insulin sensitivity enhancing agent, an insulin resistance improving agent, a retinoid-related receptor function regulating agent, a ligand for peroxisome proliferator-activated receptors, and a ligand for retinoid X receptors, etc. The term "function regulating agent" used here stands for both an agonist and an antagonist and, an agonist is preferred. The function regulating agent may be a partial agonist or a partial antagonist.

The crystals of the present invention has a blood glucose lowering action, a blood lipid lowering action, a blood insulin lowering action, an insulin sensitivity enhancing action, an insulin resistance improving action and a retinoid-related receptor function regulating action. The term "retinoid-related receptor" used here is classified as intranuclear receptors, and is a DNA-binding transcription factor whose ligand is a signal molecule such as oil-soluble vitamins, etc., and may be any of a monomer receptor, a homodimer receptor and a heterodimer receptor.

Here, examples of the monomer receptor include retinoid O receptor (hereinafter, also abbreviated as ROR) α (GenBank Accession No. L14611), RORβ (GenBank Accession No. L14160), RORγ (GenBank Accession No. U16997); Rev-erb α (GenBank Accession No. M24898), Rev-erb β (GenBank Accession No. L31785); ERRα (GenBank Accession No. X51416), ERRβ (GenBank Accession No. X51417); Ftz-Ftα (GenBank Accession No. S65876), Ftz-FIα (GenBank Accession No. M81385); TIx (GenBank Accession No. S77482), GCNF (GenBank Accession No. U14666).

Examples of the homodimer receptor include retinoid X receptor (hereinafter, also abbreviated as RXR) α (GenBank Accession No. X52733), RXRβ (GenBank Accession No. M84820), RXRγ (GenBank,Accession No. U38480); COUPα (GenBank Accession No. X12795). COUPβ (GenBank Accession No. M64497). COUPγ (GenBank Accession No. X12794); TR2α (GenBank Accession No. M29960), TR2β (GenBank Accession No. L27586); or homodimers formed by HNF4α (GenBank Accession No. X76930), HNF4γ (GenBank Accession No. Z49826), etc Examples of the heterodimer receptor include heterodimers which are formed by the above-mentioned retinoid X receptor (RXRα, RXRβ or RXTγ) and one receptor selected from retinoid A receptor (hereinafter, also abbreviated as RAR) α (GenBank Accession No. X00614). RARβ (GenBank Accession No. Y00291), RARγ (GenBank Accession No. M24857); thyroid hormone receptor (hereinafter, also abbreviated as TR) α (GenBank Accession No. M24748), TRβ (GenBank Accession No. M26747); vitamin D receptor (VDR) (GenBank Accession No. J03258); peroxisome proliferator-activated receptor (hereinafter, also abbreviated as PPAR) α (GenBank Accession No. L02932), PPARβ (PPAR δ) (GenBank Accession No. U10375), PPAR γ (GenBank Accession No. L40904)r; LXRα (GenBank Accession No. U22662), LXRβ (GenBank Accession No. U14534); FXR (GenBank Accession No. U18374); MB67 (GenBank Accession No. L29263); ONR (GenBank Accession No. X75163); and NURα (GenBank Accession No. L13740). NURβ (GenBank Accession No. X75918) and NURγ (GenBank Accession No. U12767).

The crystals of the present invention have an excellent ligand activity particularly to retinoid X receptors (RXRα, RXRβ, RXRγ) and to peroxisome proliferator-activated receptors (PPARα, PPARβ (PPARδ), PPARγ) among the above-mentioned retinoid-related receptors.

Further, the crystals of the present invention have an excellent ligand activity to peroxisome proliferator-activated receptors in heterodimer receptors formed from a retinoid X receptor and a peroxisome proliferator-activated receptor, and preferably in heterodimer receptors formed from RXRα and PPARγ.

Accordingly, the retinoid-related receptor ligand of the present invention can be used advantageously as a ligand for peroxisome proliferator-activated receptors or a ligand for retinoid X receptors.

(7) Diseases to be Treated

The crystals of the present invention and the pharmaceutical composition of the present invention can be used, for example, as an agent for preventing or treating diabetes mellitus (e.g., insulin-dependent (type 1) diabetes mellitus, noninsulin-dependent (type 2) diabetes mellitus, gestational diabetes mellitus), an agent for preventing or treating hyperlipemia (e.g., hypertriglycemia, hypercholesterolemia, hypo-high-density-lipoproteinemia, postprandial hyperlipemia), an agent for enhancing insulin sensitivity, an agent for improving insulin resistance, an agent for preventing or treating impaired glucose tolerance (IGT); and an agent for preventing progress from impaired glucose tolerance to diabetes mellitus.

Also, the crystals of the present invention and the pharmaceutical composition of the present invention can be used as an agent for preventing or treating diabetic complications (e.g., neuropathy, nephropathy, retinopathy, cataract, macroangiopathy, osteopenia, diabetic hyperosmolar coma, infectious diseases (e.g., respiratory infection, urinary tract infection, gastrointestinal tract infection, dermal soft tissue infection, inferior limb infection), diabetic gangrene, xerostomia, lowered sense of hearing, cerebrovascular disease, peripheral circulatory disturbance, etc.), obesity, osteoporosis, cachexia (e.g., carcinomatous cachexia, tuberculous cachexia, diabetic cachexia, hemopathic cachexia, endocrinopathic cachexia, infectious cachexia, cachexia induced by acquired immunodeficiency syndrome), fatty liver, hypertension, polycystic ovary syndrome, renal diseases (e.g., diabetic nephropathy, glomerular nephritis, glomerulosclerosis, nephrotic syndrome, hypertensive nephrosclerosis, terminal renal disorder), muscular dystrophy, myocardiac infarction, angina pectoris, cerebrovascular disease (e.g., cerebral infarction. cerebral apoplexy), insulin resistant syndrome, syndrome X, hyperinsulinemia, hyperinsulinemia-induced sensory disorder, tumor (e.g., leukemia, breast cancer, prostate cancer, skin cancer), irritable intestinum syndrome, acute or chronic diarrhea, inflammatory diseases (e.g., chronic rheumatoid arthritis, spondylitis deformans, osteoarthritis, lumbago, gout, postoperative or traumatic inflammation, remission of swelling, neuralgia, pharyngolaryngitis, cystitis, hepatitis (including steatohepatitis such as nonalcoholic steatohepatitis), pneumonia, pancreatitis, inflammatory colitis, ulcerative colitis), arteriosclerosis (e.g., atherosclerosis), visceral obesity syndrome, etc.

Also, the crystals of the present invention and the pharmaceutical composition of the present invention can be used for ameliorating bellyache, nausea, vomiting, or dysphoria in epigastrium, each of which is accompanied by gastrointestinal ulcer, acute or chronic gastritis, biliary dyskinesia, or cholecystitis.

Further, the crystals of the present invention and the pharmaceutical composition of the present invention can control (enhance or inhibit) appetite and food intake, and therefore, can be used as an agent for treating leanness and cibophobia (the weight increase in administration subjects suffering from leanness or cibophobia) or an agent for treating obesity.

The crystals of the present invention and the pharmaceutical composition of the present invention can be also used as an agent for preventing or treating TNF-α mediated inflammatory diseases. The TNF-α mediated inflammatory diseases mean inflammatory diseases which occur in the presence of TNF-α and can be treated by way of a TNF-α inhibitory action. Examples of such inflammatory diseases include diabetic complications (e.g., retinopathy, nephropathy, neuropathy, macroangiopathy), rheumatoid arthritis, spondylitis deformans, osteoarthritis, lumbago, gout, postoperative or traumatic inflammation, remission of swelling, neuralgia, pharyngolaryngitis, cystitis, hepatitis, pneumonia, gastric mucosal injury (including aspirin-induced gastric mucosal injury), etc.

The crystals of the present invention and the pharmaceutical composition of the present invention have an apoptosis inhibitory activity, and can be used as an agent for preventing or treating diseases mediated by promotion of apoptosis. Examples of the diseases mediated by promotion of apoptosis include viral diseases (e.g., AIDS, fulminant hepatitis), neurodegenerative diseases (e.g., Alzheimer's disease, Parkinson's disease, amyotropic lateral sclerosis, retinitis pigmentosa, cerebellar degeneration), myelodysplasia (e.g., aplastic anemia), ischemic diseases (e.g., myocardial infarction, cerebral apoplexy), hepatic diseases (e.g., alcoholic hepatitis, hepatitis B, hepatitis C), joint-diseases (e.g., osteoarthritis), atherosclerosis, etc.

The crystals of the present invention and the pharmaceutical composition of the present invention can be used for reducing visceral fats, inhibiting accumulation of visceral fats, ameliorating glycometabolism, ameliorating llpidmetabolism, ameliorating insulin resistance, inhibiting production of oxidized LDL, ameliorating lipoprotein metabolism, ameliorating coronary artery metabolism, preventing or treating cardiovascular complications, preventing or treating heart failure complications, lowering blood remnant, preventing or treating anovulation, preventing or treating hirsutism, preventing or treating hyperandrogenism, etc.

The crystals of the present invention and the pharmaceutical composition of the present invention can be used for secondary prevention and for inhibition in progress, both of various diseases described above (e.g., cardiovascular events such as myocardial infarction, etc.).

The crystals of the present invention and the pharmaceutical composition of the present invention can be used in combination with midazolam, ketoconazole, etc.

The dose of the crystals of the present invention and the pharmaceutical composition of the present invention may vary depending upon the administration subject, administering route, target disease, clinical condition, etc. and, in the case of oral administration to adults, the crystals of the present invention as an effective ingredient may be usually administered at a single dose of about 0.05 to 100 mg/kg body weight, preferably about 0.1 to 10 mg/kg body weight, more preferably about 0.2 to 4 mg/kg body weight. This dose is desirably administered once to three times a day.

(8) Combination Use of Agents

The crystals of the present invention can be used in combination with a drug such as a therapeutic agent for diabetes mellitus, a therapeutic agent for diabetic complications, an antihyperlipidemic agent, a hypotensive agent, an antiobesity agent, a diuretic agent, a chemotherapeutic agent, an immunotherapeutic agent, a therapeutic agent for osteoporosis, an antidementia agent, an erection dysfunction ameliorating agent, a therapeutic agent for incontinentia or pollakiuria, and the like (hereinafter, abbreviated as a concomitant drug). On such occasions, the time of administration of the crystals of the present invention and that of the concomitant drug is not limited. They may be administered simultaneously or at staggered times to the administration subject. The dose of the concomitant drug can be appropriately selected based on the dose which is clinically employed. The proportion of the crystals of the present invention and the concomitant drug can be appropriately selected according to the administration subject, administration route, target disease, clinical condition, combination, and other factors. In cases where the administration subject is human, for instance, the concomitant drug may be used in an amount of 0.01 to 100 parts by weight per part by weight of the crystals of the present invention.

Examples of the therapeutic agent for diabetes mellitus include insulin preparations (e.g., animal insulin preparations extracted from the bovine or swine pancreas; human insulin preparations synthesized by a genetic engineering technique using *Escherichia coli* or a yeast), insulin sensitizers (e.g., pioglitazone hydrochloride, troglitazone, rosiglitazone or its maleate, GI-262570, JTT-501, MCC-555, YM-440, KRP-297, FK-614, CS-011), α-glucosidase inhibitors (e.g., voglibose, acarbose, miglitol, emiglitate), biguanides (e.g., phenformin, metformin, buformin), sulfonylureas (e.g., tolbutamide, glibenclamide, gliclazide, chlorpropamide, tolazamide, acetohexamide, glyclopyramide, glimepiride, glipizide, glybuzole) and other insulin secretagogues (e.g., repaglinide, senaglinide, nateglinide, mitiglinide or its calcium salt hydrate, GLP-1), amyrin agonist (e.g., pramlintide), phosphotyrosine phosphatase inhibitors (e.g., vanadic acid), dipeptidylpeptidase IV inhibitors (e.g., NVP-DPP-278, PT-100, P32/98), β3 agonists (e.g., CL-316243, SR-58611-A, UL-TG-307, AJ-9677, AZ40140), gluconeogenesis inhibitors (e.g., glycogen phosphorylase inhibitors, glucose-6-phosphatse inhibitors, glucagon antagonists), SGLT (sodium-glucose cotransporter) inhibitors (e.g., T-1095).

Examples of the therapeutic agent for diabetic complications include aldose reductase inhibitors (e.g., tolrestat, epalrestat, zenarestat, zopolrestat, minalrestat, fidarestat, SNK-860, CT-112), neurotrophic factors (e.g., NGF, NT-3, BDNF), PKC inhibitors (e.g., LY-333531), AGE inhibitors (e.g., ALT946, pimagedine, pyratoxathine, N-phenacylthiazolium bromide (ALT766), EXO-226), active oxygen scavengers (e.g. thioctic acid), cerebral vasodilators (e.g., tiapuride, mexiletine).

Examples of the antihyperlipidemic agent include statin compounds which are cholesterol synthesis inhibitors (e.g., pravastatin, simvastatin, lovastatin, atorvastatin, fluvastatin, cerivastatin, itavastatin or their salts (e.g., sodium salt)), squalene synthase inhibitors or fibrate compounds (e.g., bezafibrate, clofibrate, simfibrate, clinofibrate) having a triglyceride lowering action.

Examples of the hypotensive agent include angiotensin converting enzyme inhibitors (e.g., captopril, enalapril, delapril), angiotensin II antagonists (e.g., losartan, candesartan cilexetil, valsartan, termisartan, irbesartan, tasosartan), calcium antagonist (e.g., manidipine, nifedipine, amlodipine, efonidipine, nicardipine), clonidine.

Examples of the antiobesity agent include antiobesity drugs acting on the central nervous system (e.g. dexfenfluramine, fenfluramine, phentermine, sibutramine, anfepramon, dexamphetamine, mazindol, phenylpropanolamine, clobenzorex), pancreatic lipase inhibitors (e.g. orlistat), β3 agonists (e.g. CL-316243, SR-58611-A, UL-TG-307, SB-226552, AJ-9677, BMS-196085, AZ40140), anorectic peptides (e.g. leptin, CNTF (Ciliary Neurotrophic Factor)), cholecystokinin agonists (e.g. lintitript, FPL-15849).

Examples of the diuretic agent include xanthine derivatives (e.g., theobromine and sodium salicylate, theobromine and calcium salicylate), thiazide preparations (e.g., ethiazide, cyclopenthiazide, trichlormethiazide, hydrochlorothiazide, hydroflumethiazide, benzylhydrochlorothiazide, penflutizide, polythiazide, methyclothiazide), antialdosterone preparations (e.g., spironolactone, triamterene), carbonate dehydratase inhibitors (e.g., acetazolamide), chlorobenzenesulfonamide preparations (e.g., chlorthalidone, mefruside, indapamide), azosemide, isosorbide, ethacrynic acid, piretanide, bumetanide, furosemide.

Examples of the chemotherapeutic agent include alkylating agents (e.g., cyclophosphamide, ifosamide), metabolic antagonists (e.g., methotrexate, 5-fluorouracil), antitumor antibiotics (e.g., mitomycin, adriamycin), plant-derived antitumor agents (e.g., vincristine, vindesine, Taxol), cisplatin, carboplatin, etoposide. Among these, 5-fluorouracil derivatives such as Furtulon and Neo-Furtulon are preferable.

Examples of the immunotherapeutic agent include microorganism- or bacterium-derived components (e.g., muramyl dipeptide derivatives, Picibanil), immunopotentiator polysaccharides (e.g., lentinan, schizophyllan, krestin), genetically engineered cytokines (e.g., interferons, interleukins (IL)), colonystimulating agents (e.g., granulocyte colony stimulating factor, erythropoietin), etc. Among these, IL-1, IL-2, IL-12 and the like are preferable.

Examples of the therapeutic agent for osteoporosis include alfacalcidol, calcitriol, elcaltonin, calcitonin salmon, estriol, ipriflavone, pamidronate disodium, alendronate sodium hydrate, incadronate disodium.

Examples of the antidementia agent include tacrine, donepezil, rivastigmine, galantamine.

Examples of the erection dysfunction ameliorating agent include apomorphine, sildenafil citrate.

Examples of the therapeutic agent for incontinentia or pollakiuria include flavoxate hydrochloride, oxybutynin hydrochloride, propiverine hydrochloride.

Further, agents whose effects of ameliorating cachexia have been confirmed in animal models or clinically, namely cyclooxygenase inhibitors (e.g., indomethacin) (Cancer Research, vol. 49, pp. 5935–5939, 1989). progesterone derivatives (e.g., megestrol acetate) (Journal of Clinical Oncology, vol. 12, pp. 213–225, 1994), glucocorticoids (e.g. dexamethasone), metoclopramide pharmaceuticals, tetrahydrocannabinol pharmaceuticals (the above references are applied to both), fat metabolism ameliorating agents (e.g., eicosapentanoic acid) (British Journal of Cancer, vol. 68, pp. 314–318, 1993), growth hormones, IGF-1, and antibodies to the cachexia-inducing factor TNF-α, LIF, IL-6 or oncostatin M, can also be used in combination with the crystals of the present invention.

The above concomitant drugs can be used as a mixture of two or more species in an appropriate ration. In the case of using two or more of concomitant drugs, preferable combinations include the followings.

1) an insulin sensitizer, an insulin preparation and a biguanide;
2) an insulin sensitizer, an insulin secretagogue (preferably a sulfonylurea) and a biguanide;
3) an insulin sensitizer, an insulin secretagogue (preferably a sulfonylurea) and an α-glucosidase inhibitor;
4) an insulin sensitizer, a biguanide and an α-glucosidase inhibitor;
5) an insulin sensitizer, a blood glucose lowering agent and other therapeutic agent for diabetic complications;
6) an insulin sensitizer and other two kinds of agents mentioned above;
7) an insulin sensitizer and an insulin preparation;
8) an insulin sensitizer and an insulin secretagogue (preferably a sulfonylurea);
9) an insulin sensitizer and an α-glucosidase inhibitor; and
10) an insulin sensitizer and a biguanide.

When the crystals or pharmaceutical composition of the present invention are used in combination with other agents, the amount of each agent can be reduced within a safe range by taking their adverse effect into consideration. Particularly, the dose of an insulin sensitizer, an insulin secretagogue (preferably a sulfonylurea) and a biguanide can be reduced as compared with the normal dose. Accordingly, an adverse effect which may be caused by these agents can be safely prevented. In addition, the dose of an agent for diabetic complications, an anti-hyperlipemic agent and a hypotensive agent can be reduced whereby an adverse effect which may be caused by these agents can be effectively prevented.

As hereunder, the present invention will now be illustrated in more detail by way of Reference Examples, Examples, Preparation Examples and Test Examples. However, the present invention is not limited by them. In the following Reference Examples and Examples, t means percent by weight unless otherwise mentioned.

Data of a powder X-ray crystal diffraction were determined by using RINT1100 Type (Rigakudenki, Japan) using Cu-Kα$_1$ ray (voltage: 40 KV; electric current: 40 mA) as a ray source.

REFERENCE EXAMPLE 1

Sodium borohydride (4.31 g) was gradually added to a solution of 4-(5-methyl-2-phenyl-4-oxazolylmethoxy) benzaldehyde (33.42 g) in methanol (150 ml)-tetrahydrofuran (30 ml) at 0° C. After the mixture was stirred at room temperature for 30 minutes, water was added to the reaction mixture followed by stirring for 1 hour. The precipitating crystals of 4-(5-methyl-2-phenyl-4-oxazolylmethoxy)benzylalcohol (32.85 g; yield: 98%) were collected by filtration. Recrystallization from ethyl acetate-diethyl ether gave pale yellow crystals. Melting point: 128–129° C.

REFERENCE EXAMPLE 2

Thionyl chloride (1.85 ml) was added to a solution of 4-(5-methyl-2-phenyl-4-oxazolylmethoxy)benzylalcohol (5.00 g) in toluene (40 ml) and the mixture was stirred at room temperature for 30 minutes. Ice water was added to the reaction mixture followed by extraction with ethyl acetate. The ethyl acetate layer was washed with water, dried over MgSO$_4$ and concentrated to give crystals (5.23 g; yield: 99%) of 4-(4-chloromethylphenoxymethyl)-5-methyl-2-phenyloxazole. Recrystallization from ethyl acetate-hexane gave colorless crystals. Melting point: 108–109° C.

REFERENCE EXAMPLE 3

A mixture of methyl 3-benzoylpropionate (15.0 9), hydroxylamine hydrochloride (6.50 g), sodium acetate (9.60 g) and methanol (150 ml) was heated under reflux for 8 hours. The reaction mixture was concentrated, water was added to the residue and the mixture was extracted with ethyl acetate The ethyl acetate layer was washed with water, dried (over MgSO$_4$) and concentrated. The residue was subjected to a silica gel column chromatography and, from an eluate with ethyl acetate-hexane (1:3, volume ratio), methyl (E)-4-hydroxyimino-4-phenylbutyrate (14.7 g; yield: 91%) was obtained as an oily product.

NMR (CDCl$_3$) δ: 2.58–2.67 (2H, m), 3.09–3.17 (2H, m), 3.66 (3H, s), 7.35–7.44 (3H, m), 7.56–7.67 (2H, m), 8.00–8.80 (1H, br s).

REFERENCE EXAMPLE 4

Figure 1:
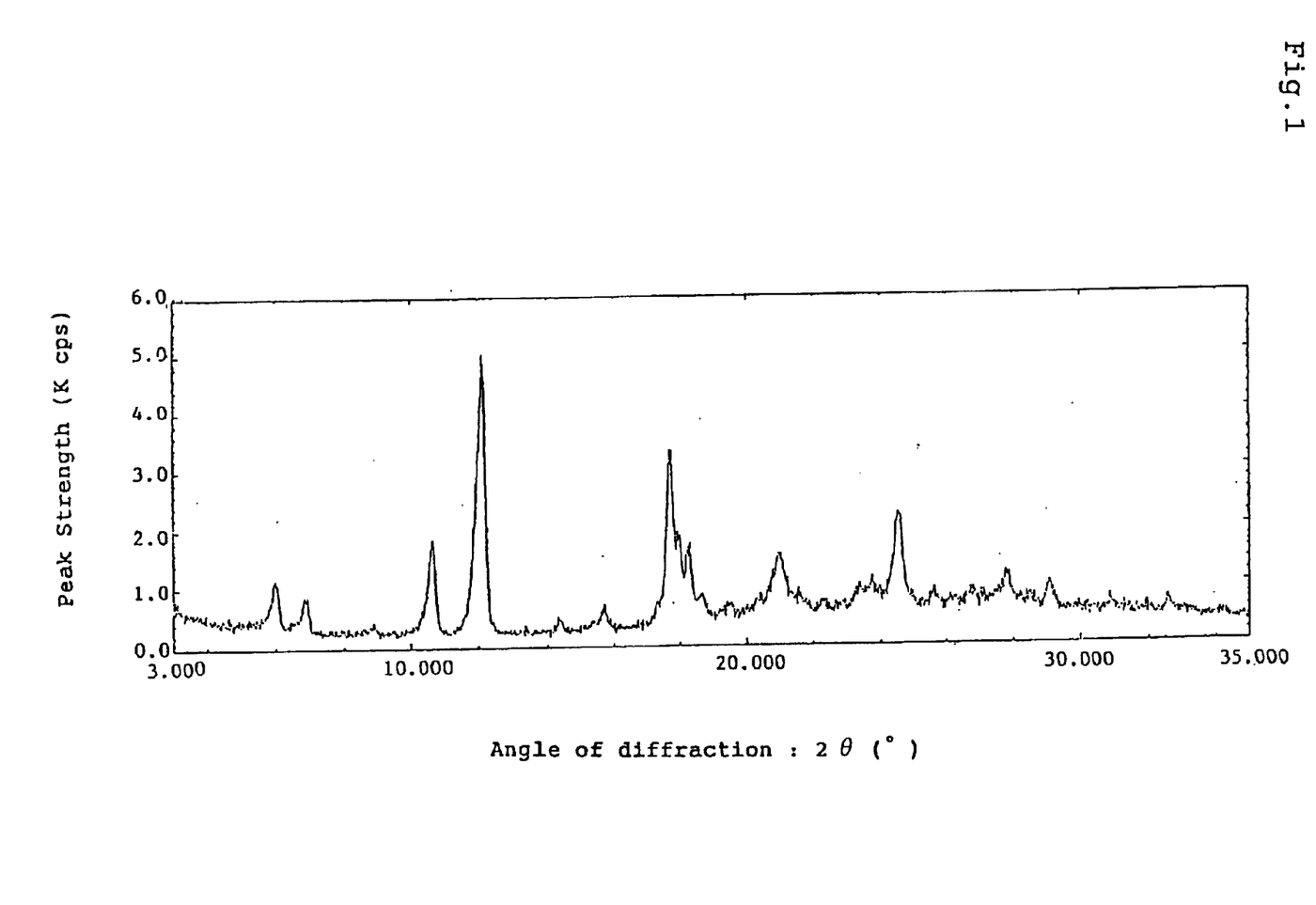
FIG. 1 shows a powder X-ray crystal diffraction pattern of the crystals obtained in Reference Example 4.

Under a nitrogen atmosphere, sodium hydride (60%; oily; 127 mg) was added to a solution of methyl (E)-4-hydroxyimino-4-phenylbutyrate (661 mg) and 4-(4-chloromethylphenoxymethyl)-5-methyl-2-phenyloxazole (1.00 g) in N,N-dimethylformamide (10 ml) at room temperature and the mixture was stirred for 1 hour. After addition of 1N hydrochloric acid (5 ml), an aqueous solution of sodium bicarbonate was added thereto, followed by extraction with ethyl acetate. The ethyl acetate layer was washed with a saturated aqueous solution of sodium chloride, dried (over MgSO$_4$) and concentrated. The residue was subjected to a silica gel column chromatography and an oily product was obtained from an eluate with ethyl acetate-hexane (1:3, volume ratio). This was dissolved in tetrahydrofuran (10 ml)-methanol (5 ml), a 1N aqueous solution of sodium hydroxide (5 ml) was added thereto and the mixture was stirred at room temperature for 1.5 hours. To the reaction solution was added 1N hydrochloric acid (5.5 ml) and the mixture was extracted with ethyl acetate. The ethyl acetate layer was washed with a saturated aqueous solution of sodium chloride, dried (over MgSO$_4$) and concentrated. The resulting crystals were recrystallized from ethyl acetate-hexane to give colorless crystals of (E)-4-[4-(5-methyl-2-phenyl-4-oxazolylmethoxy)benzyloxyimino]-4-phenylbutyric acid (907 mg; yield: 60%). The powder X-ray crystal diffraction pattern is shown in FIG. 1. Melting point: 126–127° C. (decomposition).

Elementary Analysis:
Calcd: C, 71.47; H, 5.57; N, 5.95
Found: C, 71.51; H, 5.55; N, 5.88

Data of Powder X-Ray Crystal Diffraction:

| Angle of Diffraction: 2 θ (°) | Spacing: d value (Å) |
| --- | --- |
| 5.98 | 14.8 |
| 10.7 | 8.28 |
| 12.1 | 7.30 |
| 18.0 | 4.93 |
| 21.0 | 4.23 |
| 24.6 | 3.62 |

EXAMPLE 1

Figure 2:
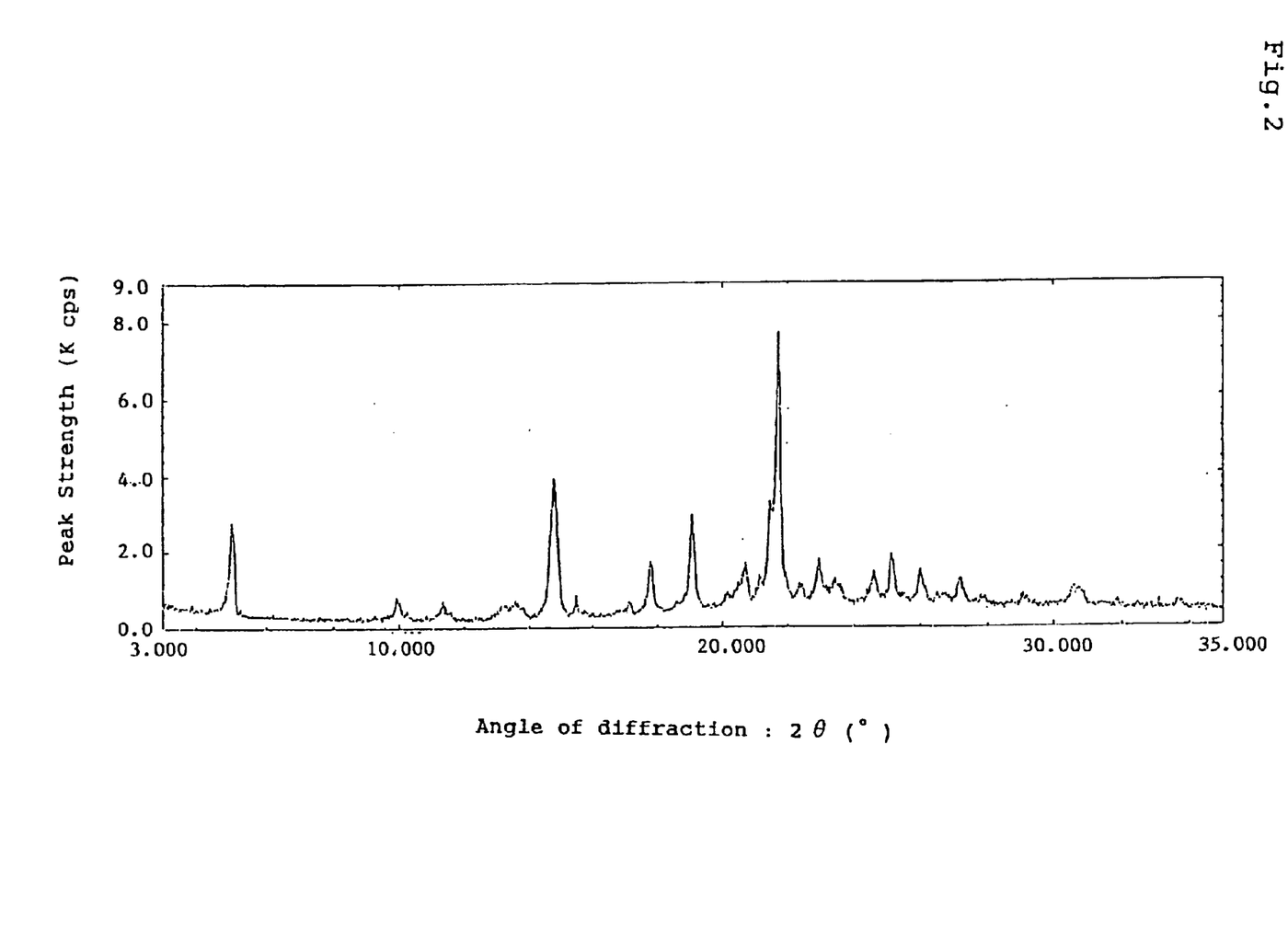
FIG. 2 shows a powder X-ray crystal diffraction pattern of the crystals obtained in Example 1.

Under a nitrogen atmosphere, sodium hydride (60%; oily; 3.00 g) was added to a solution of methyl (E)-4-hydroxyimino-4-phenylbutyrate (15.5 g) and 4-(4-chloromethylphenoxymethyl)-5-methyl-2-phenyloxazole (23.5 g) in N,N-dimethylformamide (100 ml) at 0° C. and the mixture was stirred for 2 hours. This was neutralized with 1N hydrochloric acid, aqueous solution of sodium bicarbonate was added thereto and the mixture was extracted with ethyl acetate. The ethyl acetate layer was washed with a saturated aqueous solution of sodium chloride, dried (over $MgSO_4$) and concentrated. The residue was subjected to a silica gel column chromatography and an oily product was obtained from an eluate with ethyl acetate-hexane (1:3, volume ratio). This was dissolved in tetrahydrofuran (100 ml)-methanol (50 ml), a 2N aqueous solution of sodium hydroxide (50 ml) was added thereto and the mixture was stirred at room temperature for 2 hours. The reaction mixture was neutralized with 1N hydrochloric acid and extracted with ethyl acetate. The ethyl acetate layer was washed with a saturated aqueous solution of sodium chloride dried (over $MgSO_4$) and concentrated. The resulting crystals were recrystallized from ethyl acetate-hexane to give colorless crystals of (E)-4-[4-(5-methyl-2-phenyl-4-oxazolylmethoxy)benzyloxyimino]-4-phenylbutyric acid (24.5 g; yield: 86%). Melting point: 126–127° C. A part (500 mg) of the crystals was dissolved in ethanol (5 ml) with heating and cooled at 0° C. The precipitating crystals were collected to give crystals (466 mg) showing a powder X-ray crystal diffraction pattern as given in FIG. 2. Melting point: 137–138° C.

Elementary Analysis:
Calcd: C, 71.47; H, 5.57; N, 5.95
Found: C, 71.46; H, 5.59; N, 5.94

Data of Powder X-Ray Crystal Diffraction

| Angle of Diffraction: 2 θ (°) | Spacing: d value (Å) |
|---|---|
| 5.04 | 17.5 |
| 9.92 | 8.91 |
| 11.3 | 7.81 |
| 14.8 | 5.98 |
| 19.1 | 4.65 |
| 20.7 | 4.29 |
| 21.7 | 4.09 |
| 25.1 | 3.54 |

Preparation Example 1 (Production of capsules)

| | |
|---|---|
| 1) Crystals of Example 1 | 30 mg |
| 2) Finely divided cellulose | 10 mg |
| 3) Lactose | 19 mg |
| 4) Magnesium Stearate | 1 mg |
| Total | 60 mg |

1), 2), 3) and 4) are admixed and filled into a gelatin capsule.

Preparation Example 2 (Production of tablets)

| | |
|---|---|
| 1) Crystals of Example 1 | 30 g |
| 2) Lactose | 50 g |
| 3) Corn starch | 15 g |
| 4) Carboxymethylcellulose calcium | 44 g |
| 5) Magnesium stearate | 1 g |
| 1000 tablets | 140 g |

The whole amounts of 1), 2) and 3) and 30 g of 4) are kneaded together with water and the mixture, after vacuum drying, is granulated. The granular mixture is admixed with 14 g of 4) and 1 g of 5) and the resulting mixture is tableted using a tableting machine, to give 1000 tablets each containing 30 mg of crystals of Example 1.

PREPARATION EXAMPLE 3

Production of Film-coated Tablets

[Production of a Coating Agent]

403.4 g of hydroxypropylmethylcellulose 2910 (TC-5) and 81.0 g of polyethylene glycol 6000 were dissolved in 4859.1 g of purified water. In the solution thus obtained, 54.0 g of titanium oxide and 1.620 g of yellow ferric oxide were dispersed to give a coating agent.

[Production of Plain Tablets]

A fluidized-bed granulating dryer (produced by POWREX) was charged with 576.0 g of Compound A. 2513 g of lactose, 356.4 g of corn starch and 217.8 g of croscarmellose sodium, which was admixed with preheating. Then, granulation was carried out while spraying an aqueous solution in which 138.6 g of hydroxypropylcellulose was dissolved. 3590 g of the obtained granules were milled by a Power-Mill (produced by Showa Machinery Co., Ltd.) to give pulverized powders. 3432 g of the obtained pulverized powders, 125.1 g of corn starch and 17.88 g of magnesium stearate were admixed in a tumble mixer (produced by Showa Machinery Co., Ltd.). 3410 g of the obtained mixed powders were tabletted with a tabletting machine (produced by Kikusui Seisakusho Co., Ltd.) to give plain tablets.

]Production of Film-coated Tablets]

The above coating agent was sprayed onto the obtained 27000 plain tablets in a film-coating machine (produced by POWREX) to give 27000 film-coated tablets having the following prescription and containing 16.0 mg of Compound A per tablet.

Prescription of tablets (Composition per tablet):

| (Plain tablets) | |
|---|---|
| 1) Compound A | 16.0 mg |
| 2) Lactose | 69.8 mg |
| 3) Corn starch | 13.75 mg |
| 4) Croscarmellose sodium | 6.05 mg |
| 5) Hydroxypropylcellulose | 3.85 mg |
| 6) Magnesium stearate | 0.55 mg |
| Total | 110.0 mg |
| (Film ingredients) | |
| 7) Hydroxypropylmethylcellulose 2910 | 2.988 mg |
| 8) Polyethylene glycol 6000 | 0.6 mg |
| 9) Titanium oxide | 0.4 mg |
| 10) Yellow ferric oxide | 0.012 mg |
| Total | 114.0 mg |

PREPARATION EXAMPLE 4

Production of Film-coated Tablets 27000 film-coated tablets, having the following prescription and containing 4.0 mg of Compound A per tablet, were produced in the same manner as in Preparation Example 3 except that the amount of Compound A and lactose used was 144.0 g and 2945 g, respectively.

| Prescription of tablets (Composition per tablet): | |
|---|---|
| (Plain tablets) | |
| 1) Compound A | 4.0 mg |
| 2) Lactose | 81.8 mg |
| 3) Corn starch | 13.75 mg |
| 4) Croscarmellose sodium | 6.05 mg |
| 5) Hydroxypropylcellulose | 3.85 mg |
| 6) Magnesium stearate | 0.55 mg |
| Total | 110.0 mg |
| (Film ingredients) | |
| 7) Hydroxypropylmethylcellulose 2910 | 2.988 mg |
| 8) Polyethylene glycol 6000 | 0.6 mg |
| 9) Titanium oxide | 0.4 mg |
| 10) Yellow ferric oxide | 0.012 mg |
| Total | 114.0 mg |

PREPARATION EXAMPLE 5

Production of Film-coated Tablets 27000 film-coated tablets, having the following prescription and containing 1.0 mg of Compound A per tablet, were produced in the same manner as in Preparation Example 3 except that the amount of Compound A and lactose used was 36.0 g and 3053 g, respectively.

| Prescription of tablets (Composition per tablet): | |
|---|---|
| (Plain tablets) | |
| 1) Compound A | 1.0 mg |
| 2) Lactose | 84.8 mg |
| 3) Corn starch | 13.75 mg |
| 4) Croscarmellose sodium | 6.05 mg |
| 5) Hydroxypropylcellulose | 3.85 mg |
| 6) Magnesium stearate | 0.55 mg |
| Total | 110.0 mg |
| (Film ingredients) | |
| 7) Hydroxypropylmethylcellulose 2910 | 2.988 mg |
| 8) Polyethylene glycol 6000 | 0.6 mg |
| 9) Titanium oxide | 0.4 mg |
| 10) Yellow ferric oxide | 0.012 mg |
| Total | 114.0 mg |

PREPARATION EXAMPLE 6

Production of Film-coated Tablets
[Production of a Coating Agent]
484.4 g of hydroxypropylmethylcellulose 2910 (TC-5) is dissolved in 4859.1 g of purified water. In the solution thus obtained, 54.0 g of titanium oxide and 1.620 g of yellow ferric oxide are dispersed to give a coating agent.
[Production of Film-coated Tablets]
The above coating agent is sprayed onto the 27000 plain tablets obtained in Preparation Example 3 in a film-coating machine (produced by POWREX) to give 27000 film-coated tablets having the following prescription and containing 16.0 mg of Compound A per tablet.

| Prescription of tablets (Composition per tablet): | |
|---|---|
| (Plain tablets) | |
| 1) Compound A | 16.0 mg |
| 2) Lactose | 69.8 mg |
| 3) Corn starch | 13.75 mg |
| 4) Croscarmellose sodium | 6.05 mg |
| 5) Hydroxypropylcellulose | 3.85 mg |
| 6) Magnesium stearate | 0.55 mg |
| Total | 110.0 mg |
| (Film ingredients) | |
| 7) Hydroxypropylmethylcellulose 2910 | 3.588 mg |
| 8) Titanium oxide | 0.4 mg |
| 9) Yellow ferric oxide | 0.012 mg |
| Total | 114.0 mg |

PREPARATION EXAMPLE 7

Production of Film-coated Tablets 27000 film-coated tablets, having the following prescription and containing 4.0 mg of Compound A per tablet, are produced in the same manner as in Preparation Example 4 except that the coating agent obtained in Preparation Example 6 is used.

| Prescription of tablets (Composition per tablet): | |
|---|---|
| (Plain tablets) | |
| 1) Compound A | 4.0 mg |
| 2) Lactose | 81.8 mg |
| 3) Corn starch | 13.75 mg |
| 4) Croscarmellose sodium | 6.05 mg |
| 5) Hydroxypropylcellulose | 3.85 mg |
| 6) Magnesium stearate | 0.55 mg |
| Total | 110.0 mg |
| (Film ingredients) | |
| 7) Hydroxypropylmethylcellulose 2910 | 3.588 mg |
| 8) Titanium oxide | 0.4 mg |
| 9) Yellow ferric oxide | 0.012 mg |
| Total | 114.0 mg |

PREPARATION EXAMPLE 8

Production of Film-coated Tablets 27000 film-coated tablets, having the following prescription and containing 1.0 mg of Compound A per tablet, are produced in the same manner as in Preparation Example 5 except that the coating agent obtained in Preparation Example 6 is used.

| Prescription of tablets (Composition per tablet): | |
|---|---|
| (Plain tablets) | |
| 1) Compound A | 1.0 mg |
| 2) Lactose | 84.8 mg |
| 3) Corn starch | 13.75 mg |

-continued

Prescription of tablets (Composition per tablet):

| | |
|---|---|
| 4) Croscarmellose sodium | 6.05 mg |
| 5) Hydroxypropylcellulose | 3.85 mg |
| 6) Magnesium stearate | 0.55 mg |
| Total | 110.0 mg |
| (Film ingredients) | |
| 7) Hydroxypropylmethylcellulose 2910 | 3.588 mg |
| 8) Titanium oxide | 0.4 mg |
| 9) Yellow ferric oxide | 0.012 mg |
| Total | 114.0 mg |

TEST EXAMPLE 1

Hypoglycemic and Hypolipidemic Actions in Mice

Crystals of the test compound were mixed in a powdery diet (CE-2; Japan Clea) at a concentration of 0.01%, and freely given to KKA$^y$ mice (11 weeks old; five mice in a group), a model of obesity and type 2 diabetes mellitus, for four days. During that period, water was given freely. Blood was sampled from orbital venous plexus and measurement of the components was carried out using serum. Glucose was quantified using L-type Wako Glu2 (Wako Pure Chemicals) while triglyceride was quantified using Iatro-MA701 TG kit (Iatron Laboratories Inc.). The value of treatment group is represented as percentage reduction compared with the non-treatmet group.

| Crystals of Test Compound | Hypoglycemic Action (%) | Hypolipemic Action (%) |
|---|---|---|
| Crystals of Reference Example 4 | 42 | 61 |

TEST EXAMPLE 2

Hypoglycemic and Hypolipidemic Actions in Rats

Crystals of the test compound were suspended in an amount of 1 mg/5 ml in a 0.5% methyl cellulose solution and compulsorily administered orally at the dose of 1 mg/kg/day to Wistar fatty rats (27–30 weeks old; five rats in a group), a model of obesity and type 2 diabetes mellitus, for seven days successively. During that period, diet and water were given freely. Blood was sampled from tail vein and measurement of the components was carried out using serum. Glucose was quantified using L-type Wako Glu2 (Wako Pure Chemicals) while triglyceride was quantified using L-type Wako TG.H (Wako Pure Chemical). The value of treatment group is represented as percentage reduction compared with the non-treatmet group.

| Crystals of Test Compound | Hypoglycemic Action (%) | Hypolipemic Action (%) |
|---|---|---|
| Crystals of Example 1 | 60 | 85 |

As such, the crystals of the present invention have excellent hypoglycemic and hypolipemic actions, and are useful as an agent for preventing or treating diabetes mellitus, hyperlipemia, impaired glucose tolerance, etc.

TEST EXAMPLE 3

Figure 3:
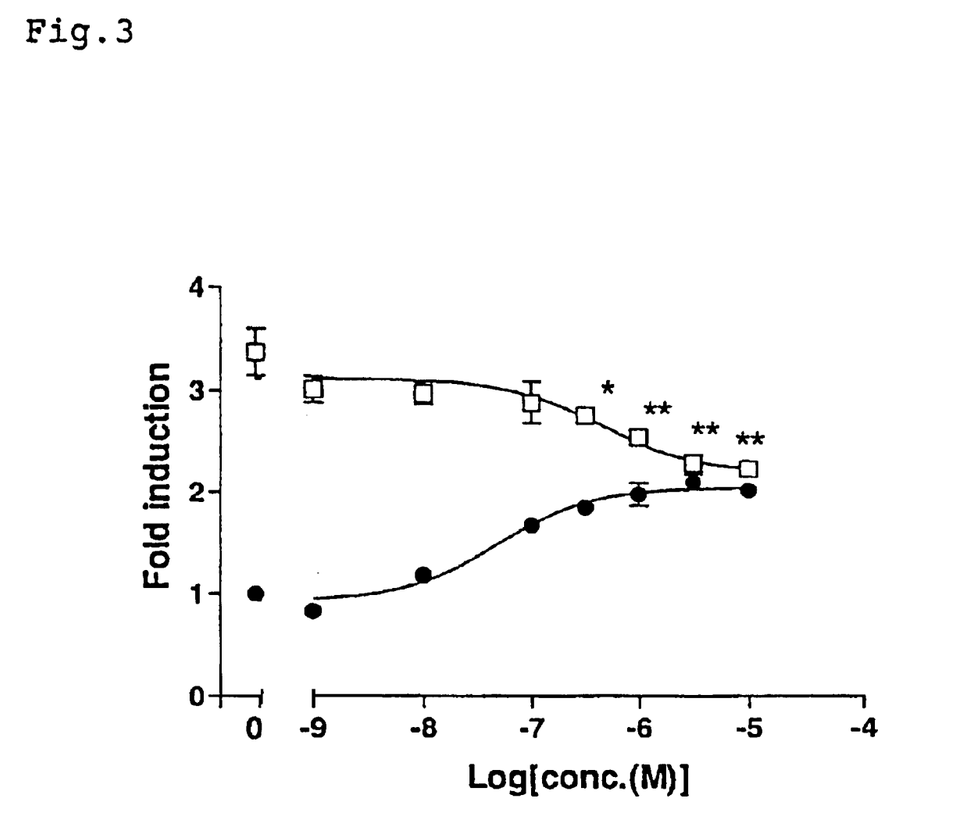
FIG. 3 shows a dose response curve showing a hPPARγ fold induction of compound A in the presence or absence of a PPARg agonist, pioglitazone.

$5\times10^6$ cells of COS-1 cells were seeded in a 150 cm$^2$ tissue culture flask, and cultivation was carried out for 24 hours, at 37° C. under 5% $CO_2$ condition. Transfection was carried out using Lipofectamine (Lifetechoriental). Namely, transfection mixture was obtained by mixing 125 $\mu$l of Lipofectamine, 100 $\mu$l of PLUS Reagent, an intranuclear receptor-expression plasmid, 2.5 $\mu$g each of hPPARγ-expression plasmid and hRXRα-expression plasmid, 5 $\mu$g of a reporter plasmid and 5 $\mu$g of pRL-CMV (Promega) with 25 ml of opti-MEM (Lifetechoriental). COS-1 cells were incubated in 25 ml of the transfection mixture for 3 hours, at 37° C. under 5% $CO_2$ condition. Then, 25 ml of DMEM medium (Nikken Biomedical Institute) containing 0.1% fatty acid free-BSA (Wako Pure Chemical) was added, and cultivation was further carried out for 24 hours, at 37° C. under 5% $CO_2$ condition. The transfected cells were collected, and suspended in DMEM medium (Nikken Biomedical Institute) containing 0.1% fatty acidfree-BSA (Wako Pure Chemical), which was poured into each well of a 96-well white plate (Corning) by 90 $\mu$l ($2\times10^4$ cells). Then, 10 $\mu$l of compound A (final concentration: 1 nM to 10 $\mu$M) was added in the presence or absence of 10 mM pioglitazone, and cultivation was carried out for 48 hours, at 37° C. under 5% $CO_2$ condition. After the culture medium was removed from the 96-well white plate (Corning), 40 $\mu$l of Pikkagene LT7.5 was added and stirred. Then, a luciferases activity was determined using 1420 ARVO Multilabel Counter (wallac company). Based on the obtained luciferases activity, fold induction was calculated when a luciferases activity in a control group in which no compound was added was defined as 1. The results are shown in FIG. 3. In FIG. 3, ● shows a group treated with compound A, □ shows a group treated with compound A and pioglitazone. The fold induction shows mean±standard error (SE) (n=3).

As shown in FIG. 3, the maximum fold induction of compound A was 45% of that of pioglitazone, a PPARγ agonist, which shows that compound A is a partial agonist of PPARγ. Further, compound A dose dependently inhibited activation by 10 $\mu$M of pioglitazone to the level of the maximum fold induction of compound A, which shows that compound A is a partial antagonist.

INDUSTRIAL APPLICABILITY

The crystals of the present invention are stable, have an excellent antidiabetic action, show a low toxicity, and therefore, are useful as a medicine.

The crystals of the present invention are excellent in physical/chemical properties (e.g., melting point, solubility, stability) and biological properties (e.g., pharmacokinetics (absorption, distribution, metabolism, excretion), pharmacodynamics), and therefore, are quite useful as a medicine.

What is claimed is:

1. Crystals of (E)4-[4-(5-methyl-2-phenyl-4-oxazolylmethoxy)benzyloxyimino]-4-phenylbutyric acid which have a melting point of about 136° C. to about 139° C., or pharmacologically acceptable salts thereof.

2. Crystals of (E)4-[4-(5-methyl-2-phenyl-4-oxazolylmethoxy)benzyloxyimino]-4-phenylbutyric acid showing diffraction patterns having characteristic peaks at the spacings (d values) of about 17.5 and about 6.0 Å by a powder x-ray crystal diffraction, or pharmacologically acceptable salts thereof.

3. A pharmaceutical composition comprising the crystals or salts as defined in claim 1 or claim 2 together with a pharmacologically acceptable carrier.

4. The pharmaceutical composition according to claim 3, which is an agent for treating diabetes mellitus.

5. The pharmaceutical composition according to claim 3, which is an agent for treating hyperlipemia.

6. The pharmaceutical composition according to claim 3, which is an agent for treating impaired glucose tolerance.

7. The pharmaceutical composition according to claim 3, which is an agent for treating inflammatory diseases.

8. The pharmaceutical composition according to claim 3, which is an agent for treating arteriosclerosis.

9. The pharmaceutical composition according to claim 3, which is an insulin sensitivity enhancing agent.

10. The pharmaceutical composition according to claim 3, which is an insulin resistance improving agent.

11. A method for treating diabetes mellitus in a mammal in need thereof, which comprises administering to said mammal an effective amount of crystals or salts as defined in claim 1 or claim 2.

12. A method for producing a pharmaceutical composition, which comprises mixing the crystals or salts as defined in claim 1 or claim 2 together with a pharmacologically acceptable carrier.

13. A method for regulating retinoid-related receptor function in a mammal in need thereof, which comprises administering to said mammal an effective amount of crystals or salts as defined in claim 1 or claim 2.

14. The method according to claim 13, wherein the retinoid-related receptor is a peroxisome proliferator-activated receptor.

15. The method according to claim 13, wherein the retinoid-related receptor is a retinoid X receptor.

* * * * *